United States Patent [19]

Horváth et al.

[11] Patent Number: 4,622,222

[45] Date of Patent: Nov. 11, 1986

[54] PROCESS FOR THE PREPARATION OF A LYOPHILIZED VACCINE AGAINST DUCK VIRUS HEPATITIS

[75] Inventors: Erzsébet Horváth, Budapest; Gábor Tollas, Gödöllö, both of Hungary

[73] Assignee: Phylaxia Oltoanyagtermelo Vallalat, Budapest, Hungary

[21] Appl. No.: 449,745

[22] Filed: Dec. 14, 1982

[30] Foreign Application Priority Data

Dec. 23, 1981 [HU] Hungary .............................. 3935/81

[51] Int. Cl.$^4$ .......................... A61K 39/12; C12N 7/00
[52] U.S. Cl. ........................................ 424/89; 435/235
[58] Field of Search ........................... 424/89; 435/235

[56] References Cited

U.S. PATENT DOCUMENTS 4,302,444 11/1981 Baxendale .............................. 424/89

FOREIGN PATENT DOCUMENTS 2126957 12/1972 Fed. Rep. of Germany ........ 424/89

OTHER PUBLICATIONS

Asplin, F. D., *An Attenuated Strain of Duck Hepatitis Virus*, The Veterinary Record, Dec. 27, 1958, pp. 1226–1230.
Biological Abstracts 73:61184, (1982).
Biological Abstracts 72:24311, (1981).
C A B Abstracts I0040-67195.
Hwang et al., Avian Diseases, 1964, 19,8, pp. 264–268.
Zvbtsova, State Control Inst. for Vet. Preparations, Zvenigorodsk oe Shosse 5, Moscow D-22.
Asplin F. D. and McLauchlan J. D.: Vet. Rec. 1954, 66, p. 456.
Asplin F. D., Vet. Rec., 1956, 68, p. 412.

*Primary Examiner*—Robert J. Warden
*Assistant Examiner*—Shawn P. Foley
*Attorney, Agent, or Firm*—Karl F. Ross; Herbert Dubno

[57] ABSTRACT

The invention relates to a process for the preparation of the lyophilized vaccine against duck hepatitis by using the attenuated hepatitis virus TN cultivated by Asplin.

According to the invention the virus deposited in the Strain Collection of the Hungarian Institute of Public Healts under No. 00220 is injected into the allantoic cavity of embryonated SPF-hen's eggs, the eggs are incubated at a temperature of about 37° C., the embryos died between 24 and 96 hours are collected, homogenized with a physiological saline solution, antibiotics are added to the pure suspension, and after the addition of protective and skeleton forming agents the sterile virus material is lyophilized in a manner known per se.

The lyophilized vaccine can be stored at a temperature of +4° C. for one year in contradiction to the known liquid vaccine storable in freezed state at a temperature of −20° C. for half a year and which has to be used within 7 days from the delivery (with a storage temperature of +4° C.). The titre of the vaccine prepared according to the invention is at least tenfold of that of the known vaccine, thus much less embryonated eggs are used for the process according to the invention what means cost saving. Due to the lyophilization the vaccine can be transported to far destinations, too, what was not possible at the known liquid product stored in freezed state.

3 Claims, No Drawings

PROCESS FOR THE PREPARATION OF A LYOPHILIZED VACCINE AGAINST DUCK VIRUS HEPATITIS

FIELD OF THE INVENTION

The invention relates to a process for the preparation of a lyophilized vaccine against duck hepatitis by using the attenuated hepatitis virus TN cultivated by Asplin.

BACKGROUND OF THE INVENTION

Duck hepatitis is a dangerous viral disease to which ducklings are susceptible in the first 4–5 weeks of their life. If they are not protected against this disease, 40 to 50% of the young animals can perish. Therefore a protection method was sought and a vaccine suitable for immunization was developed. For the preparation of the presently used vaccine the attenuated TN virus cultivated by Asplin is used (Asplin F. D. and McLauchlan J. D.: Vet. Rec. 1954, 32, 66, 456; Asplin F. D.: Vet. Rec. 1956, 68, 412). The virus whose titer has to be at least $10^4$ $EID_{50}/ml$, is injected into the allantoic cavity of 10-day embryonated hen's egg in a dilution between 1:10 and 1:20; the eggs are candled daily and the eggs containing deceased embryos are taken out and destroyed in the first 24 hours. Eggs are suitable for the preparation of the vaccine in which the embryo died between 24 and 96 hours after the inoculation. The allantoamniotic fluid of the eggs (that is the fluid surrounding the embryo) is drawn off with vacuum, treated with antibiotics and filled into bottles.

The process was doubtlessly a great advance in the field of intensive large-scale poultry breeding. However the vaccine possesses disadvantages. The main disadvantage is that it is fluid and has to be stored in frozen state at a temperature of at least $-20°$ C. The substance can be stored in this state for at most half a year. In the course of transport of the frozen vaccine interruptions often occur; therefore it is preferred to transport the vaccine personally to the destination. After melting (calculated from the time of the delivery) it can be stored at a temperature of $+4°$ C. for 7 days. The vaccine is suitable for use if its titer reaches the value of $10^{3.5} EID_{50}/ml$. According to our own examinations this vaccine cannot by lyophilized, although tests were carried out with numerous protective materials. The virus loss caused by the lyophilization is too high, the biological activity of the lyophilized substance is not sufficient.

At the production of this vaccine the material consumption is very high; for the preparation of 100 liters of vaccine, 23,000 embryonated hen eggs are necessary.

OBJECTS OF THE INVENTION

The aim of the invention was to elaborate a process for producing a vaccine of high titer by using less raw material, which is lyophilizable and storable for a longer time and—due to its dry state—readily transportable.

DESCRIPTION OF THE INVENTION

In the present invention we started from the fact that the quantity of the virus multiplying in the embryonated hen egg is not the same at all of the different parts of the egg (Hwang J. and Dougherty E.: Avian Dis. 1964, 19, 8, 264). The virus enriches mainly in the body of the chicken embryo, particularly in the liver, while just the allantoamniotic fluid—the material from which the traditional vaccine is isolated—contains the least virus.

In the face of this problem a process for the preparation of a lyophilized vaccine against duck hepatitis was developed by using the attenuated hepatitis virus TN cultivated by Asplin. According to the invention the virus deposited in the Strain Collection of the Hungarian Institute of Public Health under No. 00220 is injected into the allantoic cavity of 10-day embryonated SPF-hen eggs, the eggs are incubated at a temperature of about 37° C., the embryos died after the inoculation between the 24 and 96 hours are collected, optionally the harder parts of them are eliminated under sterile conditions, then the embryos are homogenized with physiological saline solution, centrifuged, antibiotics are added to the pure suspension and after the addition of protective and skeleton forming agents the virus substance is freeze-dried by well-known methods.

The SPF (specific pathogen free) eggs for the present process must be free from Avian encephalomyelitis, fowl plague, EDS, bronchitis, leucosis A–B, Gumboro, Marek, Reovirus as well as from Salmonella Gall., Salmonella typhi murium, Mycoplasma Gall., Mycoplasma Synoviae and the antibodies of these, respectively.

Under homogenization the suspension is advantageously diluted to such an extent that the substance consists of 25 to 35% by volume of embryo and 75 to 65% by volume of physiological saline solution.

It is particularly advantageous to use a combination of polyvinylpyrrolidone, gelatine, glucose and saccharose as protective and skeleton forming agent.

At the lyophilization one proceeds advantageously so that the material receiving shelves of the freeze-drying machine are precooled to a temperature between $0°$ and $-6°$ C., the substance placed on the shelves is cooled to a temperature between $-30°$ and $-40°$ C., the water in the substance is sublimated in vacuum, after the sublimation the shelves are heated to a temperature between $+30°$ and $+40°$ C. and thus the substance is dried for 4 to 10 hours.

In the process of the invention, the virus is inoculated in diluted state into the allantoic cavity of the 10-day embryonated SPF-egg in a dose of 10,000 $EID_{50}$ per egg. After the inoculation the embryos deceased within the first 24 hours are developed. The eggs are candled daily, collected in the 48th, 72nd and 96th hour, the eggs containing the dead embryos are stored until use at a temperature of $+4°$ C. The front part of the embryo head (eyes, bill) is removed under sterile conditions, the bill because it is hard and the eyes because they discolour the vaccine.

The embryos are smashed in a mixer, then they are further homogenized in an ultra-homogenizer (e.g. in an ultraturrax machine) while physiological saline solution is added. The suspension contains about 50 to 80% by volume of physiological saline solution calculated to its total quantity. The suspension is centrifuged with a speed of rotation of 2000–3000 $minutes^{-1}$ for 20 minutes, then the clear middle part is filtered through four layers of gauze after the bone residues on the bottom of the centrifuge glass and the feather fundaments swimming on the top of the substance have been removed. In order to examine the purity of the filtered substance it is spread on culture-media and treated with antibiotics (penicillin, streptomycin, neomycin and chloramphenicol). If the substance proves to be infected after a certain time, gentamycin is added. The sterile substance is lyophilized within 5-6 days from harvesting; in the meantime it is stored at +4° C.

Before the lyophilization skeleton forming and protective agents are added to the virus suspension. E.g. the following combination is advantageous:

5% of collidone solution (polyvinylpyrrolidone, 10% by volume)
5% of gelatine solution (10% by volume)
4% of glucose solution (50% by volume)
3% of saccharose solution (50% by volume).

The lyophilization can be carried out by well-known methods. It will be described in the examples in detail.

The inoculum strain virus is prepared similarly as the vaccine but here the sterility has to be attained to a maximum because no antibiotic can be added to the inoculum virus.

The lyophilized vaccine can be stored at a temperature of +4° C. for one year.

Considering the fact that the titer of the virus suspension after lyophilization is at least by one magnitude higher than that of the vaccine which has to be stored in freezed state, the quantity to be prepared is reduced to a tenth. Due to this fact many fewer eggs are used; note that the price of the embryonated eggs amounts to 95% of the production cost. At the same time a significant saving of labor is attained.

In dependence upon the virus titer, by diluting a 2 ml vial 100 to 1000 single doses can be obtained according to the following relation:

| titre | Number of doses | Necessary quantity of buffer for the dilution: ducklings | Necessary quantity of buffer for the dilution: laying ducks |
|---|---|---|---|
| $10^5$ $EID_{50}$/ml | 100 | 10 ml | 100 ml |
| $10^{5.3}$ $EID_{50}$/ml | 200 | 20 ml | 200 ml |
| $10^{5.7}$ $EID_{50}$/ml | 500 | 50 ml | 500 ml |
| $10^6$ $EID_{50}$/ml | 1000 | 100 ml | 1000 ml |

The dose in case of both the duckling and the laying duck is at least 2000 $EID_{50}$ that means that due to the different dilution 0.1 ml of vaccine in the case of duckling and 1 ml of vaccine in the case of laying duck is added. The vaccine can be administered as injection or—in the case of ducklings, in the drinking water. It is recommended to inoculate the breeding stock twice before the laying period. The laying ducks pass the immunity to the ducklings through the yolk but the thus-obtained protection lasts only for about 14 days, therefore the ducklings, too, have to be treated. If the vaccine is added to the drinking water, it is recommended to have the stock thirsted for some hours and to give the vaccinic water only after it. By the moving of the animals it has to be ensured that every duckling can drink and such drinking vessels should be used in which the ducklings cannot bath.

The invention is illustrated in detail by the following examples.

EXAMPLE 1

Preparation and lyophilization of the vaccine 10-day embryonated hen's egg of SPF quality are candled, the limit of the air-sack and the place of the embryo are marked on the shell, then the blunt end of the egg is disinfected. The suspension of the egg-inoculation virus prepared with sterile physiological saline solution is injected into the allantoic cavity through a hole made above the air-sack. 0.2 ml of the substance containing approximately 50,000 $EID_{50}$ virus quantity per milliliter is used for each egg. Then the hole is closed with paraffin and the eggs are incubated in hatchers at 37° C. The embryos dying within the first 24 hours as well as those still living after 96 hours are destroyed. The eggs are candled daily and the eggs containing the dead embryos are stored between +2° C. and +5° C. until use.

Under sterile conditions the embryos are collected, the front part of the head is cut off with a pair of scissors, then the embryos are smashed in a mixer and diluted with physiological saline solution, they are squashed still further in an ultraturrax homogenizer. The embryo squash is further diluted while the obtained suspension contains 70% of physiological saline solution. This suspension is centrifuged at a speed of rotation of 3000 $minutes^{-1}$ for 20 minutes and the clear middle part is filtered through four layers of sterile gauze.

The thus-obtained material is submitted to a purity examination, then directly after the examination it is treated with antibiotics by using 100,000 IU of penicillin, 760,000 IU of streptomycin, 0.2 g. of chloramphenicol and 0.5 g of neomicyn for one liter of suspension. The treated suspension is allowed to stand at room temperature for one hour, then it is inoculated on culture media which is suitable for cultivation of aerob and anaerob bacteria as well as fungi. If within 3 days no growth of a microorganism begins on the culture media kept at room temperature, respectively in a thermostat, the material is considered sterile. If it proves infected, 0.3 g. of gentamycin per liter is added to it. The suspension is lyophilized as quickly as possible, but at least within 5-6 days after harvesting. Until that time it is stored at a temperature of +4° C. Before the lyophilization the following sterile protective agents are added to the suspension:

5% of collidone solution (10% by volume)
5% of gelatine solution (10% by volume)
4% of glucose solution (50% by volume)
3% of saccharose solution (50% by volume).

The total quantity of the protective and skeleton forming agents amounts to 17%. Before the lyophilization the titer of the suspension is determinated: $10^7$ $EID_{50}$/ml.

The virus suspension is filled in doses of 2 ml into vials and is placed upon the material-receiving shelves of the freeze-drying machine precooled to a temperature of −5° C. When the temperature of the material is reduced to −45° C., the vacuum pump is operated. When the pressure decreased to 0.1 mbar, the heating of the material-receiving shelves is begun and adjusted so that the temperature of the material should be between −30° and 35° C. (for a pressure of 0.1 mbar a shelf temperature of about −15° C. is needed). When the sublimation is finished, the shelves are heated to a temperature of +35° C. and the maximum vacuum is put on so the material should be desiccated as much as possible. After 8 hours drying time the water content of the product is under a value of 2%. The vials are stoppered while still in the lyophilizer under vacuum and the rubber stopper is protected by metal stop-cap.

EXAMPLE 2

Preparation of the inoculation virus

One proceeds as in Example 1, with the difference that no antibiotic is added to the suspension and the ready material is not lyophilized but stored in deep-frozen state in liquid nitrogen. Its titer is at least $10^{6.5}$–$10^{7}$ $EID_{50}$/ml. Before use a dilution is prepared from the inoculation virus in a ratio of 1:60 to 1:200; 0.2 ml of which contain about 10,000 $EID_{50}$ of the virus. The inoculation virus cannot haemagglutinate the erythrocytes of the hen.

EXAMPLE 3

Detection of the immune state

For lack of an appropriate virulent virus the immune state was evaluated with the help of a virus neutralization test carried out with serum. The 480 test ducklings came from a farm where the breeding stock was not immunized due to export interests. One group consisted of 20 test animals.

In the vaccination tests PBS buffer of the following composition was used for the dilution:

| | |
|---|---|
| NaCl | 8 g |
| KCl | 0.2 g |
| $Na_2HPO_4.2H_2O$ | 1.15 g |
| $KH_2PO_4$ | 0.2 g |
| $CaCl_2$ | 0.1 g |
| $MgCl_2.6H_2O$ | 0.1 g |
| distilled water ad | 1,000.0 ml |

Different dilutions were prepared from the vaccine prepared according to Example 1 with the buffer of the above composition, and immunization tests were carried out by injecting the dilutions subcutaneously or added the vaccine in water. For comparison tests were carried out with the traditional liquid vaccine, too.

12 days after the immunization blood samples were taken and the serum was inactivated at 56° C. for 30 minutes, and the antibody level was determined with the virus dilution method. The dilution of the serum in a ratio of 1:10 was mixed with the individual virus dilutions, and the thus-prepared mixtures were allowed to stand at room temperature for 1 hour and then injected into 11-day embryonated SPF-eggs. The virus titre and the neutralization index (NI), respectively, were determined on the basis of the number of embryos which died or were still living, but showed characteristic pathological alterations after one week and it was calculated by Reed-Muench method. The results were summarized in the following table:

| Method of treatment | Dose $EID_{50}$ | Type of administration | NI | Difference relative to the control in % |
|---|---|---|---|---|
| control | — | — | 1.6 | — |
| liquid vaccine | 50 | subcut. | 2 | 25 |
| | 613 | subcut. | 3 | 87.5 |
| | 6130 | subcut. | 3.6 | 125 |
| lyophilized vaccine | 158 | subcut. | 2.6 | 62.5 |
| according to the | 1585 | subcut. | 4.6 | 187.5 |
| invention | 15850 | subcut. | 4.8 | 200 |
| lyophilized vaccine | 3160 | watering | 3.7 | 131 |
| according to the | 31600 | watering | 4.4 | 175 |
| invention | 316000 | watering | 4.6 | 187.5 |

An index above 2 is already positive; an index above 3 is considered as a very good result. From the table it is clear that the protective effect of the vaccine of the invention is excellent.

EXAMPLE 4

Proving of the storability of the vaccine

The storability of the vaccine was examined by modelling the real storage as well as by usual thermal load. In the modelling of the storage we started from the fact that in most countries the vaccines have to be stored at a temperature of +4° C. according to regulations, thus the product marked for the export, too, was examined under such conditions. The vaccine stored at a temperature between +2° and +5° C. lost 0.6 exponent (from the exponent of $EID_{50}$) of the activity within 12 months, an irrelevant loss, but corresponds to the scattering among the virus contents of the vials.

The thermal load test renders possible a certain fast examination. If the titer of the vaccine stored at 37° C. for 1 week is still appropriate, it is certain that it can be used for one year when stored according to the regulations. The vaccine prepared according to the invention lost 0.5 exponent of activity when stored at 37° C. for 1 week what is a very advantageous result.

We claim:

1. A process for the preparation of a lyophilized vaccine against duck hepatitis comprising the steps of:

(a) injecting a hepatitis virus TN as deposited in the Strain Collection of the Hungarian Institute of Public Health under No. 00220, into the allantoic cavity of embryonated SPF hen eggs;

(b) incubating the eggs at a temperature of about 37° C.;

(c) collecting the embryos dying between 24 and 96 hours from the start of incubation;

(d) discarding the embryos dying prior to 24 and subsequent to 96 hours form the start of incubation;

(e) homogenizing the collected embryos in physiological saline solution to form a suspension;

(f) centrifuging the suspension;

(g) adding to the suspension an antibiotic selected from the group consisting of penicillin, streptomycin, chloramphenicol, neomycin, gentamycin, and mixtures thereof in an amount sufficient to sterilize said suspension, and adding to the suspension a protective skeleton-forming agent consisting essentially of:

5% of collidone solution,

5% of gelatin solution,

4% of glucose solution, and

3% of sucrose solution, so that the total quantity of the protective skeleton-forming agents in the suspension is 17% by weight; and (h) lyophilizing the resulting composition.

2. A lyophilized vaccine against duck hepatitis made by the steps of:

(a) injecting a hepatitis virus TN as deposited in the strain collection of the Hungarian Institute of Public Health under No. 00220, into the allantoic cavity of embryonated SPF hen eggs;

(b) incubating the eggs at a temperature of about 37° C.;

(c) collecting the embryos dying between 24 and 96 hours from the start of incubation;

(d) discarding the embryos dying prior to 24 and subsequent to 96 hours from the start of incubation;

(e) homogenizing the collected embryos in physiological saline solution to form a suspension;

(f) centrifuging the suspension;

(g) adding to the suspension an antibiotic selected from the group consisting of penicillin, streptomycin, chloramphenicol, neomycin, gentamycin, and mixtures thereof in an amount sufficient to sterilize said suspension, and adding to the suspension a protective skeleton-forming agent consisting essentially of:

5% of collidone solution,
5% of gelatin solution,
4% of glucose solution, and
3% of sucrose solution, so that the total quantity of the protective skeleton-forming agents in the suspension is 17% by weight; and (h) lyophilizing the resulting composition.

3. A method of incubating ducks against duck hepatitis which comprises administering to the ducks an effective amount of the vaccine prepared by the steps of:

(a) injecting a hepatitis virus TN as deposited in the strain collection of the Hungarian Institute of Public Health under No. 00220, into the allantoic cavity of embryonated SPF hen eggs;

(b) incubating the eggs at a temperature of about 37° C.;

(c) collecting the embryos dying between 24 and 96 hours from the start of incubation;

(d) discarding the embryos dying prior to 24 and subsequent to 96 hours from the start of incubation;

(e) homogenizing the collected embryos in physiological saline solution to form a suspension;

(f) centrifuging the suspension;

(g) adding to the suspension an antibiotic selected from the group consisting of penicillin, streptomycin, chloramphenicol, neomycin, gentamycin, and mixtures thereof in an amount sufficient to sterilize said suspension, and adding to the suspension, a protective skeleton-forming agent consisting essentially of:

5% of collidone solution;
5% of gelatin solution,
4% of glucose solution,
3% of sucrose solution, so that the total quantity of the protective skeleton-forming agents in the suspension is 17% by weight; and (h) lyophilizing the resulting composition.

* * * * *